(12) United States Patent
Ikeda et al.

(10) Patent No.: US 10,465,160 B2
(45) Date of Patent: Nov. 5, 2019

(54) METHOD FOR PRODUCING DRY MICROBIAL CELL POWDER

(75) Inventors: Masakazu Ikeda, Tokyo (JP); Hiroshi Ishikawa, Kanagawa (JP); Kisaku Shimura, Tokyo (JP); Yuki Fukuda, Tokyo (JP); Masahiko Ito, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 14/111,657

(22) PCT Filed: Apr. 12, 2012

(86) PCT No.: PCT/JP2012/060007
§ 371 (c)(1),
(2), (4) Date: Oct. 14, 2013

(87) PCT Pub. No.: WO2012/141244
PCT Pub. Date: Oct. 18, 2012

(65) Prior Publication Data
US 2014/0038269 A1 Feb. 6, 2014

(30) Foreign Application Priority Data
Apr. 14, 2011 (JP) .................. 2011-089736

(51) Int. Cl.
*C12N 1/16* (2006.01)
*C12N 9/96* (2006.01)
(Continued)

(52) U.S. Cl.
CPC ............... *C12N 1/16* (2013.01); *C12N 1/04* (2013.01); *C12N 9/2468* (2013.01); *C12N 9/2471* (2013.01); *C12N 9/96* (2013.01)

(58) Field of Classification Search
None
See application file for complete search history.

(56) References Cited

U.S. PATENT DOCUMENTS 2,773,002 A * 12/1956 Connors .......... C12Y 302/0102
426/34
4,857,469 A * 8/1989 Ishimura .............. C12P 41/005
435/138

(Continued)

FOREIGN PATENT DOCUMENTS

CN 1173974 A 2/1998
EP 2 711 416 A1 3/2014

(Continued)

OTHER PUBLICATIONS

Eiji Ishikawa, Takafumi Sakai, Haruo Ikemura, Keisuke Matsumoto, and Hiroshi Abe, Identification, Cloning, and Characterization of a Sporobolomyces singularis β-Galactosidase-like Enzyme Involved in Galacto-Oligosaccharide Production, 2005, Journal of Bioscience and Bioengineering, vol. 99, No. 4, pp. 331-339.*

(Continued)

*Primary Examiner* — Renee Claytor
*Assistant Examiner* — Trent R Clarke
(74) *Attorney, Agent, or Firm* — Oblon, McClelland, Maier & Neustadt, L.L.P.

(57) ABSTRACT

An object of the present invention is to develop a means capable of maintaining the enzymatic activity of a microorganism even in a dry state. Provided is a method for producing a dry microbial cell powder maintaining an enzyme titer, characterized by comprising adding a carbohydrate to a liquid of microbial cells having an enzymatic activity and then drying the liquid. Also provided is a dry microbial cell powder obtained by the method.

3 Claims, 2 Drawing Sheets

(51) Int. Cl.
*C12N 1/04* (2006.01)
*C12N 9/38* (2006.01)

(56) References Cited

U.S. PATENT DOCUMENTS

| | | | |
|---|---|---|---|
| 5,294,546 A * | 3/1994 | Dombou et al. | 435/101 |
| 6,010,725 A | 1/2000 | Meister et al. | |
| 2010/0247503 A1 * | 9/2010 | Galindo Fentanes et al. | 424/93.462 |

FOREIGN PATENT DOCUMENTS

| | | |
|---|---|---|
| JP | 5 58714 | 3/1993 |
| JP | 7 203950 | 8/1995 |
| JP | 9 19283 | 1/1997 |
| JP | 10 57031 | 3/1998 |
| JP | 2002 17337 | 1/2002 |
| JP | 4071037 | 11/2003 |
| JP | 2006 223268 | 8/2006 |
| JP | 2008 43206 | 2/2008 |

OTHER PUBLICATIONS

NPL document 'NSD 300'—a screenprint of the Google translation of webpage http://www.sanei-toka.co.jp/product/product.php?c=38 accessed Jul. 17, 2015, online since Mar. 1, 1003 according to Google.*

NPL document "Torulopsis", a webpage from Mycobank at http://www.mycobank.org/Biolomics.aspx?Table=Mycobank&MycoBankNr_=278539, accessed Feb. 6, 2016.*

The NPL document "Lactose Percentages of Dairy Products" is available at http://www.stevecarper.com/li/list_of_lactose_percentages.htm, accessed Jan. 3, 2017.*

Ananta, E., Birkeland, S. E., Corcoran, B., Fitzgerald, G. F., Hinz, S., Klijn, A., Matto, J., Mercernier, A., Nilsson, U., Nyman, M., et al., Processing effects on the nutritional advancement of probiotics and prebiotics, 2004, Microbial Ecology in Health and Disease, vol. 16, Issue 2-3, pp. 113-124.*

Bernice D. Karlton-Senaye, Reza Tahergorabi, Valerie L. Giddings & Salam A. Ibrahim, Effect of gums on viability and b-galactosidase activity of *Lactobacillus* spp. in milk drink during refrigerated storage, 2014, International Journal of Food Science and Technology, vol. 50, Issue 1, pp. 32-40.*

Combined Chinese Office Action and Search Report dated May 13, 2014 in Patent Application No. 201280011040.5 (with English language translation).

Yun Guo, et al., "Survival of Lactobacillus fermentum KLDS1.0709 after spray-drying", Key Laboratory of Dairy Science, Ministry of Education, Food Science & Technology College, Northeast Agricultural University, vol. 32, No. 02, (2011), pp. 109-111 (with English abstract).

Lodato, P., et al., "Viability and thermal stability of a strain of *Saccharomyces cerevisiae* freeze-dried in different sugar and polymer matrices", Appl. Microbiol. Biotechnol., vol. 52, pp. 215-220, (1999).

Nomura, Y., et al., "Preparation and Preservation of Freeze-dried Cells of Acetic Acid Bacteria with Aldehyde Oxidase Activity", Bisci. Biotechnol. Biochem., vol. 62, No. 6, pp. 1134-1137, (1998).

Boza, Y., et al., "Effect of spray-drying on the quality of encapsulated cells of *Beijerinckia* sp", Process Biochemistry, vol. 39, pp. 1275-1284, (2004).

Boza, Y., et al., "Exopolysaccharide production by encapsulated *Beijerinckia* cultures", Process Biochemistry, vol. 39, pp. 1201-1209, (2004).

International Search Report dated Jun. 12, 2012 in PCT/JP12/060007 Filed Apr. 12, 2012.

Extended Search Report dated Dec. 11, 2014 in European Patent Application No. 12771834.4.

Takafumi Sakai, et al., "Repeated-batch production of galactooligosaccharides from lactose at high concentration by using alginate-immobilized cells of Sporobolomyces singularis YIT 10047", J. Gen. Appl. Microbiol., 54, 2008, pp. 285-293.

* cited by examiner

METHOD FOR PRODUCING DRY MICROBIAL CELL POWDER

TECHNICAL FIELD

The present invention relates to a method for producing a dry microbial cell powder, more particularly relates to a dry microbial cell powder capable of maintaining the enzymatic activity of a microorganism stably for a long period of time in a dry state regardless of whether the microorganism is viable or dead, and also to a method for producing the same.

BACKGROUND ART

There are many microorganisms that have a useful enzymatic activity, and such microorganisms are widely used in the production of functional food materials such as carbohydrates, amino acids, and phospholipids. Among these, there are known many microorganisms which can be used in the production of carbohydrate materials, particularly oligosaccharides, and for example, it has been reported that a galactooligosaccharide is produced by utilizing the β-galactosidase activity of yeast belonging to the genus *Sporobolomyces singularis* (PTL 1). It has also been reported that a mutant microorganism in which the β-galactosidase activity of *Sporobolomyces singularis* has been increased was created (PTL 2).

It is, however, difficult in terms of technology and cost to industrially release and purify the above-described β-galactosidase of *Sporobolomyces singularis* since the enzyme is tightly bound to the cell walls of the microorganism, like some other enzymes produced by microorganisms. Therefore, when β-galactosidase of *Sporobolomyces singularis* is industrially utilized, it is supplied in the form of a dilute microbial cell liquid, however, utilization form poses a problem.

Namely, the utilization form has the following problems: the storage and distribution costs are too expensive because the dilute microbial cell liquid has such form that it contains water, a buffer, etc. in an amount several times more than the amount of the microbial cells; it is difficult to control microbial contamination because of the liquid form and such form is not suitable for a long-term storage; and in order to decrease the risk of microbial contamination, it is necessary to produce the product on a demand-led basis.

In particular, it is essential to come up with a solution to the above-given problems in order to produce industrially a galactooligosaccharide at low cost using β-galactosidase of *Sporobolomyces singularis*, and the development of a means of maintaining the enzymatic activity of a microorganism even in a dry state has been desired.

CITATION LIST

Patent Literature

PTL 1: JP-B-5-58714
PTL 2: Japanese Patent No. 4071037
PTL 3: JP-A-10-57031
PTL 4: JP-A-2002-17337

SUMMARY OF INVENTION

Technical Problem to be Solved by the Invention

Accordingly, an object of the invention is to provide a method for producing a dry microbial cell powder capable of maintaining the enzymatic activity of a microorganism stably for a long period of time in a dry state.

Means for Solving the Problem

The inventors of the present application made intensive studies in order to solve the above-described problems, and as a result, they found that the enzymatic activity of a microorganism can be maintained for a long period of time in a state where dry microbial cells and a carbohydrate coexist regardless of whether the dry microorganism is viable or dead.

Further, they also found that in the case where the dry microbial cell powder is prepared by a spray drying method, by adding a carbohydrate to a microbial cell liquid in advance, and then spray drying the liquid, the enzyme titer hardly decreases during drying.

Still further, they found that by utilizing these properties, it is possible to culture a microorganism freely from the constraints of the demand-led basis, and moreover, the cost of distribution can be greatly reduced, and thus the present invention has been completed.

That is, the invention is directed to a method for producing a dry microbial cell powder maintaining an enzyme titer, characterized by including adding a carbohydrate to a microbial cell liquid having an enzymatic activity and then drying the liquid.

Further, the invention is directed to a dry microbial cell powder which can be stored for a long period of time, containing microbial cells having an enzymatic activity and a carbohydrate.

Effects of Invention

According to the invention, there is obtained a microbial cell powder in which the enzymatic activity of a microorganism is hardly decreased even when stored for as long as 1 year or longer, which is economically extremely efficient from the viewpoints of both distribution and production. Further, in the method of the invention, even if dead cells are used as the microorganism, the enzyme titer thereof can be maintained, and therefore, it is possible to avoid deterioration of quality due to a metabolite or the like produced by the microorganism which is caused in the case where viable cells are used. The dry microbial cell powder obtained by the method of the invention can be used in the production reaction of oligosaccharides without any practical problems.

DESCRIPTION OF EMBODIMENTS

In the method of the invention, the microorganism from which the dry microbial cell powder is obtained may be of any kind as long as it is a microorganism such as a bacterium, yeast, or a fungus, and an enzyme is bound to cell walls or an enzyme is intracellularly produced, and also may be a microorganism undergone various treatments. Examples of the bacterium include *Streptococcus thermophilus, Lactobacillus bulgaricus, Streptococcus lactis, Lac-* tobacillus salivarius, Lactobacillus leichmannii, Lactobacillus helveticus, Bacillus brevis, Bacillus stearothermophilus, Bifidobacterium bifidum, Bifidobacterium breve, Bifidobacterium longum, and Bifidobacterium adolescentis. Further, the enzyme is not particularly limited, and for example, when the enzyme is a carbohydrate degrading enzyme, examples thereof include amylase, sucrase, α- and β-galactosidases, glucoseisomerase, α- and β-glucosidases, β-fructofuranosidase, α- and β-mannosidases, and xylanase. Among these microorganisms, yeast which produces β-galactosidase is preferred.

Examples of the yeast which produces β-galactosidase among the above-described microorganisms include yeast belonging to the genus *Sporobolomyces*, the genus *Kluyveromyces*, the genus *Lipomyces*, the genus *Candida*, the genus *Cryptococcus*, the genus *Sterigmatomyces*, the genus *Bullera*, the genus *Bensingtonia*, the genus *Ballistosporomyces*, the genus *Fellomyces*, the genus *Filobasidium*, the genus *Sirobasidium*, the genus *Tilletiopsis*, the genus *Itersonilia*, the genus *Tilletia*, the genus *Saccharomyces*, the genus *Schizosaccharomyces*, the genus *Hansenula*, the genus *Rhodotorula*, the genus *Debaryomyces*, the genus *Pichia*, and the genus *Torulopsis*, and in particular, the genus *Sporobolomyces*, the genus *Sterigmatomyces*, the genus *Kluyveromyces*, the genus *Cryptococcus*, the genus *Rhodotorula*, the genus *Sirobasidium*, and the genus *Lipomyces* are preferred, and more preferred is any of the microorganisms belonging to the genus *Sporobolomyces*, the genus *Cryptococcus*, the genus *Rhodotorula*, and the genus *Sirobasidium*, particularly preferred is *Sporobolomyces singularis*, *Sterigmatomyces elviae*, *Cryptococcus laurentii*, *Rhodotorula lactosa*, *Rhodotorula minuta*, *Sirobasidium magnum*, or *Lipomyces lipofer*, and furthermore preferred is *Sporobolomyces singularis*, *Cryptococcus laurentii*, *Rhodotorula lactose*, *Sirobasidium magnum*, or *Rhodotorula minuta*.

As an example of the yeast which is more preferably used, *Sporobolomyces singularis* can be given, and *Sporobolomyces singularis* JCM 5356, which is an example thereof, is available upon payment from RIKEN BioResource Center (3-1-1, Kouyadai, Tsukuba-shi Ibaraki-ken, 305-0074, Japan).

Further, as another example, yeast obtained as a β-galactosidase high-producing mutant microorganism by a production method described in PTL 2 can be given. Among these, as specific examples of yeast obtained by the steps (a) to (c) in the above-described patent literature using *Sporobolomyces singularis* JCM 5356 as a parent strain, *Sporobolomyces singularis* ISK-#4D4, ISK-#5A5, and ISK-##2B6 can be given, and these strains have been deposited dated Apr. 10, 2002 at International Patent Organism Depositary, National Institute of Advanced Industrial Science and Technology (Chuo 6, Higashi 1-1-1, Tsukuba-shi, Ibaraki-ken, 305-8566, Japan) under accession Nos. FERM P-18818, FERM P-18819, and FERM P-18817, respectively.

In the method of the invention, first, a microbial cell liquid is prepared by culturing a microorganism according to a common procedure, and then, collecting the microbial cells using, for example, a De Laval continuous centrifuge, a membrane concentrating device, or the like, followed by washing.

Subsequently, to this microbial cell liquid, a carbohydrate is added as a stabilizing agent according to a common procedure, followed by drying. More specifically, in the case where spray drying is used, a necessary amount of carbohydrate is added to the microbial cell liquid in which the microorganism is suspended, and the liquid in such a state is spray-dried, whereby a target dry microbial cell powder can be obtained. The amount of the cells in the microbial cell liquid is not particularly limited, but is preferably from 1 to 10 mass/vol % (hereinafter simply expressed in "%"), more preferably from 2 to 6%. Further, the carbohydrate to be used is not particularly limited, and a monosaccharide, a disaccharide, a tri- or higher oligosaccharide, or a polysaccharide can be used, and examples of the monosaccharide include glucose, galactose, fructose, and mannose, examples of the disaccharide include lactose, lactose isomers, maltose, sucrose, and trehalose, examples of the tri- or higher oligosaccharide include various oligosaccharides such as galactooligosaccharides, maltooligosaccharides, and fructooligosaccharides, and examples of the polysaccharide include dextrins and starch. Among these, from the viewpoints of an effect of stabilizing the enzyme titer, ease of drying, and cost, at least one carbohydrate selected from the group consisting of lactose, maltose, and a dextrin is preferred, in particular, it is preferred to use lactose and/or maltose, and it is more preferred to use lactose.

In this case, the amount of the carbohydrate to be added to the microbial cell liquid is not particularly limited, however, from the viewpoint of an effect of stabilizing the enzyme titer, the amount is preferably 0.1% or more, more preferably 0.5% or more, further more preferably 1% or more with respect to the amount of the microbial cell liquid. On the other hand, if the amount of the carbohydrate to be added to the microbial cell liquid is too large, the enzyme titer per unit weight of the dry microbial cell powder is decreased, and therefore, the amount of the carbohydrate is preferably 30% or less, more preferably 15% or less, further more preferably 10% or less, still further more preferably 5% or less, yet still further more preferably 3% or less. In view of this, the amount of the carbohydrate to be added to the microbial cell liquid is preferably from 0.1 to 30%, more preferably from 0.5 to 15%, further more preferably from 0.5 to 10%, still further more preferably from 1 to 10%, yet still further more preferably from 1 to 5%, particularly preferably from 1 to 3% with respect to the amount of the microbial cell liquid.

In the case where the carbohydrate can be a substrate for the enzyme (for example, in the case where lactose is added as a stabilizing agent to a liquid of microbial cells which produce β-galactosidase), there may be cases where part or most of the carbohydrate is subjected to a reaction during addition of the carbohydrate to completion of spraying, however, the effect of the carbohydrate is exhibited regardless of the degree of reaction (the degree of degradation or the degree of polymerization), and therefore, this is not much of a problem. For example, after the carbohydrate is added, even if a reaction is performed at 5° C. to 40° C. for about 1 hour to 40 hours, there is no problem at all from the viewpoint of stabilization of the enzyme titer.

Further, in the case where the carbohydrate can be a substrate for the enzyme, there may be a case where the added carbohydrate is subjected to an enzymatic reaction, which means that a carbohydrate different from the added carbohydrate is contained in the dry microbial cell powder in addition to the added carbohydrate, however, this is of no problem at all from the viewpoint of stabilization of the enzyme titer. Examples of the carbohydrate contained in the dry microbial cell powder include monosaccharides, disaccharides, tri- or higher oligosaccharides, and polysaccharides, and examples of the monosaccharide include glucose, galactose, fructose, and mannose, examples of the disaccharide include lactose, lactose isomers, maltose, sucrose, and trehalose, examples of the tri- or higher oligosaccharide include various oligosaccharides such as galactooligosaccharides and fructooligosaccharides, and examples of the polysaccharide include dextrins and starch. Further, as the carbohydrate contained in the dry microbial cell powder in the case of using lactose as the carbohydrate to be added to the microbial cell liquid, glucose, galactose, lactose, a lactose isomer, and a galactooligosaccharide can be exemplified; as the carbohydrate contained in the dry microbial cell powder in the case of using maltose, glucose, maltose, and a maltooligosaccharide can be exemplified; and as the carbohydrate contained in the dry microbial cell powder in the case of using a dextrin, glucose, maltose, a maltooligosaccharide, and a dextrin can be exemplified. Since it is preferred to use at least one carbohydrate selected from the group consisting of lactose, maltose, and a dextrin as the carbohydrate to be added to the microbial cell liquid, it is preferred that in the dry microbial cell powder, at least one carbohydrate selected from the group consisting of glucose, galactose, lactose, a lactose isomer, a galactooligosaccharide, maltose, a maltooligosaccharide, and a dextrin is contained. Further, since it is more preferred to use lactose and/or maltose as the carbohydrate to be added to the microbial cell liquid, it is more preferred that in the dry microbial cell powder, at least one carbohydrate selected from the group consisting of glucose, galactose, lactose, a lactose isomer, a galactooligosaccharide, maltose, and a maltooligosaccharide is contained. Further, since it is more preferred to use lactose as the carbohydrate to be added to the microbial cell liquid, it is further more preferred that at least one carbohydrate selected from the group consisting of glucose, galactose, lactose, a lactose isomer, and a galactooligosaccharide is contained.

As for the conditions for spray drying, the inlet and outlet temperatures of a drying chamber may be in a range in which the enzyme is not significantly inactivated, and further, the rotation speed of an atomizer, the feeding amount of a stock solution, etc. hardly affect the final enzyme titer, although a dry microbial cell powder having slightly different properties as a product is obtained depending on such conditions, and therefore, it is not necessary to pay much attention to such conditions. Specifically, the inlet temperature of a drying chamber can be, for example, from 70° C. to 200° C., preferably from 110° C. to 180° C., and the outlet temperature of a drying chamber can be, for example, from 50° C. to 120° C., preferably from 70° C. to 90° C. Further, the rotation speed of an atomizer can be, for example, from 10,000 to 30,000 rpm, and the feeding amount of a stock solution can be, for example, from 0.2 to 200 kg/hour. The spray drying can also be performed using a spraying system such as a two-fluid nozzle other than an atomizer. Incidentally, by using a spray drying method, almost all the microorganisms are killed in this drying step, thereby obtaining a dry microbial cell powder with few viable cells, and therefore, the spray drying method is preferred.

On the other hand, in the case where a lyophilization method is used, a necessary amount of a carbohydrate is added to the microbial cell liquid, and then, the liquid may be lyophilized according to a common procedure. The addition amount of the carbohydrate in this case is also preferably from 0.1 to 30%, more preferably from 0.5 to 15%, further more preferably from 0.5 to 10%, still furthermore preferably from 1 to 10%, yet still further more preferably from 1 to 5%, particularly preferably from 1 to 3% with respect to the amount of the microbial cell liquid.

The dry microbial cell powder obtained as described above can maintain the enzymatic activity of the microorganism stably for a long period of time in a dry state. The microorganism may be either viable cells or dead cells, however, in consideration of a decrease in quality due to a metabolite or the like produced by the microorganism, the microorganism is preferably dead cells.

The dry microbial cell powder obtained as described above contains the carbohydrate in an amount 0.01 to 30 times, preferably 0.05 to 15 times, more preferably 0.05 to 10 times, further more preferably 0.1 to 10 times, still further more preferably 0.1 to 5 times, yet still furthermore preferably 0.1 to 3 times more than the amount of the dry microbial cells. Further, the amount of water contained therein is not particularly limited, but desirably 10% by mass or less. The enzyme titer after drying is preferably 70% or more of the enzyme titer before drying, and in the case where the drying method is spray drying, the suppression of a decrease in enzyme titer can be achieved only by the above-described method. In the case of lyophilization, unlike spray drying, the enzyme titer is not decreased even by drying, and therefore, only the microbial cells are lyophilized into a powder, and to the resulting powder, the carbohydrate in the form of a powder may be added.

The dry microbial cell powder obtained according to the invention has a specific effect that it maintains the enzyme titer of the microorganism immediately after drying over 1 year or longer even when stored at room temperature (25° C.). That is, it can maintain a high enzyme titer which is 50% or more, and further 80 to 90% or more of the enzyme titer immediately after drying for a long period of time.

Heretofore, it has been known to use lactose or the like for increasing the survival rate of a microorganism or as an excipient (PTL 3 and PTL 4), however, the method of the invention is not at all intended to increase and maintain the survival rate of a microorganism as described in the patent literature, and is based on a different technical thought. In the invention, it is preferred that the microorganism itself is killed and only the enzymatic activity of the microorganism is maintained.

EXAMPLES

Next, the invention will be described in more detail with reference to Examples, however, the invention is by no means limited to these Examples. In the following Examples, the β-galactosidase titer, the ratio of a residual water amount to a solid content, a particle size distribution, and the viable cell count of *Sporobolomyces singularis* were determined by the following methods.

(1) Method for Measurement of β-Galactosidase Titer (a) Preparation of Test Liquid In the case where a test sample is a concentrate liquid, about 2.5 g thereof, and in the case where a test sample is a dry product, about 150 to 350 mg thereof was placed in a 50-mL centrifugal tube, and the sample placed therein was accurately weighed, and suspended in a 50 mM sodium phosphate-citric acid buffer solution (pH 4.0) (hereinafter referred to as "buffer solution"). Then, washing was performed by centrifuging the resulting suspension (20000 G, 15 mins) to remove the carbohydrate. After this washing procedure was performed 3 times, the washed material was transferred to a 50-mL measuring flask, brought to a constant volume with the buffer solution, and well suspended therein, whereby a test liquid was prepared.

(b) Measurement

In a 100-mL measuring flask, 0.3766 g of o-nitrophenyl-β-D-galacto-pyranoside (ONPG) was weighed, dissolved in the buffer solution and brought to a constant volume, whereby a 12.5 mM ONPG solution was prepared. In a test tube, 0.8 mL of this ONPG solution was placed, and the test tube was maintained in a thermoregulated water bath at 30° C. for 5 minutes. Thereto, 0.2 mL of the test liquid was added and mixed well, and a reaction was allowed to proceed at 30° C. for 10 minutes. Then, 4 mL of a 0.25 M sodium carbonate solution was added to stop the reaction (a test system). Separately, in a test tube, 0.8 mL of the ONPG solution and 4 mL of a 0.25 M sodium carbonate solution were placed, and further 0.2 mL of the test liquid was added thereto and mixed well (a blank system). Each of the test system and the blank system was centrifuged (2000 G, 10 mins, 15 to 20° C.), and the absorbance of the resulting supernatant was measured at a wavelength of 420 nm, and then, the number of units was calculated according to the following formula. The amount of the enzyme required for releasing 1 μmol of o-nitrophenol (ONP) in 1 minute under the above-described reaction conditions was determined as 1 U.

$$\text{Activity value}^* = \frac{A_1 - A_2}{0.91} \times \frac{1}{0.2} \times \frac{1}{10} \times B \quad \text{[Math. 1]}$$

$A_1$: absorbance of test liquid $A_2$: absorbance of blank $B$: dilution ratio

*: U/g or U/ml

Further, in the case where the β-galactosidase titer per dry solid content was calculated, the calculation was performed using a solid content determined by the following method.
(2) Ratio of Residual Water Amount to Solid Content The residual water in the dry microbial cell powder (hereinafter referred to as "dry product") obtained by spray drying was measured using an infrared aquameter manufactured by Kett Electric Laboratory under the conditions of 105° C. for 15 minutes. Further, the solid content in the lyophilized product and the solid contents in a stock solution to be dried and in the dry product to be used when the β-galactosidase titer per solid content is calculated were calculated from the weight of a dry material after a treatment at 105° C. for 16 hours.
(3) Particle Size Distribution The particle size distribution of the spray-dried product was measured by a dry process using a laser diffraction particle size distribution analyzer (HELOS & RODOS system) manufactured by Sympatec, Inc.
(4) Viable Cell Count of *Sporobolomyces Singularis*

Lactose (2.5%), yeast extract (0.5%), monopotassium phosphate (0.1%), magnesium sulfate (0.05%), and agar (1.5%) were dissolved in water, and the pH of the resulting solution was adjusted to 5.0 with 2 N hydrochloric acid. Then, the solution was sterilized by autoclaving (121° C., 10 mins), and a flat plate (φ 90 mm) was prepared. On this plate, 100 μL of a sample dissolved and diluted with physiological saline was plated, and cultured at 25° C. for about 1 week. The resulting colonies were counted and the obtained value was determined as the viable cell count of *Sporobolomyces singularis*.

Example 1

Preparation of Dry Yeast Cell Powder

*Sporobolomyces singularis* YIT 10047 (ISK-##2B6, hereinafter referred to as "Ss") was aerobically cultured at 27° C. for 4 days in a medium (pH 5) containing glucose (5%), yeast extract (0.6%), monopotassium phosphate (0.1%), and magnesium sulfate (0.05%). This culture solution was centrifuged (10000 G, 30 mins) to obtain wet cells, and sterilized tap water was added thereto and the wet cells were well suspended therein. The resulting suspension was centrifuged under the same conditions, and the obtained wet cells were suspended in a small amount of tap water, and the thus obtained suspension was used as an Ss concentrate liquid (solid content: 4.9%). To 20 L of the Ss concentrate liquid, 5 L of a 25% lactose solution was added, and the resulting mixture was stirred well, whereby a stock solution to be dried was obtained. This procedure was performed at 20° C. or lower. By using this stock solution to be dried as a sample, a yeast powder was prepared by a lyophilization method or a spray drying method. The solid content (calculated value) in the stock solution to be dried includes Ss at about 3.9% and lactose at about 5%.

The spray drying was performed by using a pilot apparatus (PRODUCTION MINOR, GEA Process Engineering, Inc.) attached with a rotary atomizer under various operational conditions. The operational conditions are shown in Table 1.

Further, the lyophilization was performed by using a lyophilizer RLE-206 (Kyowa Vacuum Engineering Co., Ltd.) under the conditions that the shelf temperature was 25 to 30° C.

For the dry products obtained by spray drying and lyophilization, a storage test was performed as follows. Each dry product was placed in a reclosable plastic bag and then, the bag was hermetically sealed and stored in a thermoregulated chamber at 5° C. or 25° C. for about 1 year. A portion thereof was taken out at regular intervals, and the β-galactosidase titer thereof was measured.

Physiological Test after Spray Drying:

Regarding the dry products obtained by spray drying, the specific drying conditions therefor and the evaluation results of the obtained dry products are shown in Table 1. In the case of SD-1 to SD-3, the particle size of the dry product was tried to be changed by decreasing the rotation speed of the rotary atomizer to increase the size of the liquid droplet. In the case of SD-4, the production efficiency was tried to be increased by raising the drying temperature by 5° C. and increasing the feeding amount. The conditions for the spray drying and the results of the obtained products are shown in Table 1.

TABLE 1

|  |  | SD-1 | SD-2 | SD-3 | SD-4 |
|---|---|---|---|---|---|
| Rotation speed of atomizer (rpm) | | 25000 | 18000 | 15000 | 18000 |
| Feeding amount of stock solution (kg/hr) | | 4.0 | 4.0 | 4.0 | 5.0 |
| Inlet temperature of drying chamber (° C.) | | 115 | 115 | 115 | 120 |
| Outlet temperature of drying chamber (° C.) | | 80 | 80 | 80 | 80 |
| Product | State | Sphere | Sphere | Sphere | Sphere |
| | Average particle size (μm) | 15 | 18 | 21 | 17 |
| | Residual water content (%) | 3.6 | 4.0 | 5.0 | 5.5 |
| | Residual titer ratio (%) | 96.7 | 95.7 | 94.6 | 96.0 |

As apparent from these results, the residual titer ratios (the ratio of the titer per solid content in the dry product to the titer per solid content in the stock solution to be dried) after drying of SD-1 to SD-3 were all as high as about 95%, which was determined to be a practically applicable level. Also in the case of SD-4, in which the drying temperature was raised by 5° C., a significant difference in residual titer ratio was not observed.

In the case of spray drying Ss, if the Ss concentrate liquid is dried as such, the β-galactosidase titer per solid content is significantly decreased, and therefore, it was revealed that the enzyme titer could be maintained high by adding lactose when drying.

Further, SD-1 to SD-3 were confirmed such that the average particle size was increased as the rotation speed of the atomizer was decreased.

Further, although the data are not shown, by using these dry products, the production reaction of oligosaccharides was performed on a laboratory scale, and it was confirmed that the change in sugar composition over time, the time required until completion, etc. were equivalent to those in the case of using the Ss concentrate liquid before the drying treatment.

Storage Test for Dry Product:

For the spray dried product and the lyophilized product, a storage test was performed at 5° C. or 25° C. for about 1 year. As the spray-dried product, two samples: SD-2 and SD-4, in which the drying temperature was different, were used, and as the lyophilized product, two samples prepared from the Ss concentrate liquid "without lactose: FD(−)" and the stock solution to be dried "with 5% lactose: FD(+)" were used. For each sample, sampling was performed on a daily basis, and the residual titer ratio (the ratio of the titer per solid content in the dry product after storage to the titer per solid content in the dry product immediately after drying) was calculated. The results of the spray dried products are shown in Table 2 and FIG. 1, and the results of the lyophilized products are shown in Table 3 and FIG. 2.

Figure 1:
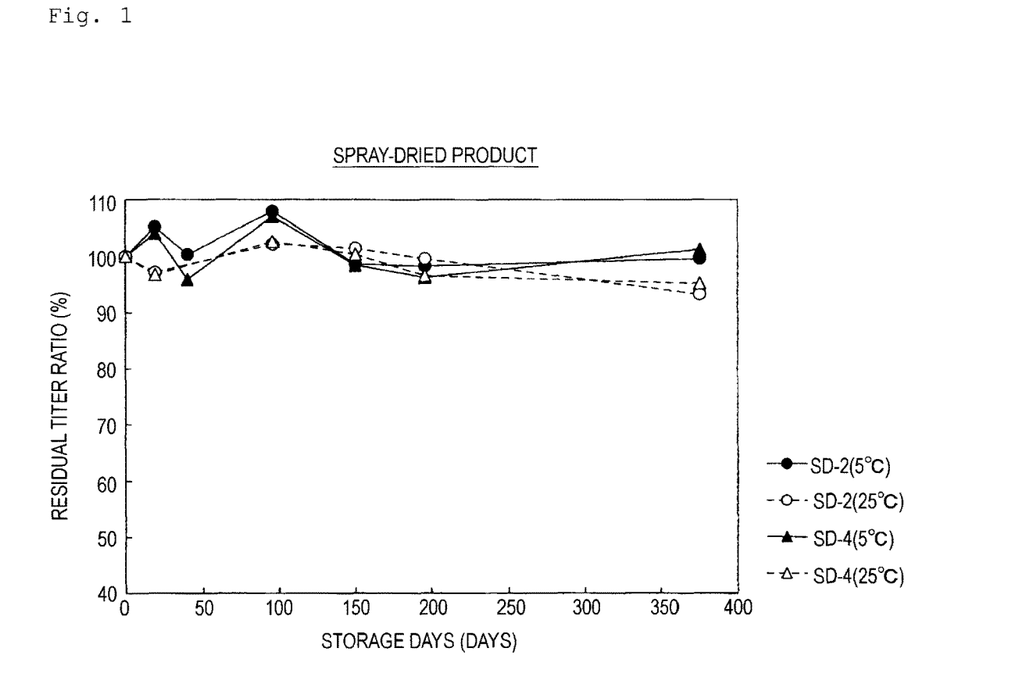
FIG. 1 is a view showing the results of a 1-year storage test for spray-dried products.

From the results shown in Table 2 and FIG. 1, as for the storage of the spray-dried products, the stability was equivalent between SD-2 and SD-4, and the residual titer ratio after 1 year was almost 100% of that at the time of initiation of the test in the case of storage at 5° C., and even in the case of storage at 25° C., the residual titer ratio was maintained at about 95% after 1 year. From these results, it was found that the titer stability of the spray-dried product was extremely high. It was confirmed that the ability to produce an oligosaccharide of the four types of spray-dried products after 1 year storage was equivalent to that before storage.

Figure 2:
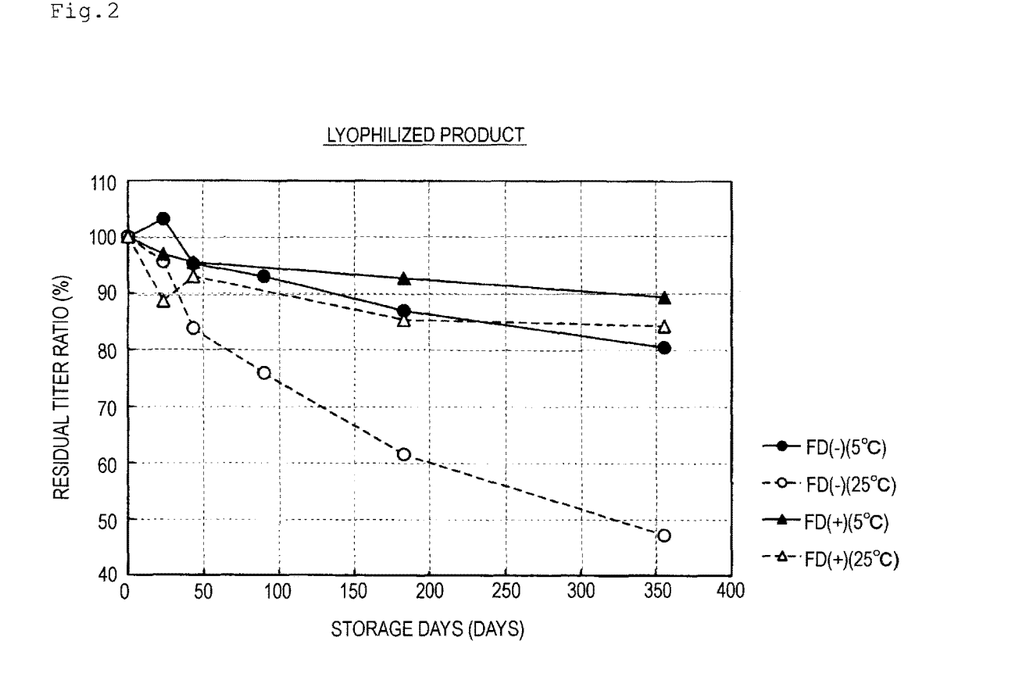
FIG. 2 is a view showing the results of a 1-year storage test for lyophilized products.

Further, from the results shown in Table 3 and FIG. 2, also in the case of the storage of the lyophilized product, the presence or absence of the stabilizing agent (lactose) has an effect on the residual titer ratio, and the residual titer ratio in the case of FD(+) in which lactose was added was higher than that in the case of FD(−) in which lactose was not added under both temperature conditions of 5° C. and 25° C., and the residual titer ratio after 1 year storage was about 85 to 90%.

TABLE 2

|  | SD-2 (5° C.) | SD-2 (25° C.) | SD-4 (5° C.) | SD-4 (25° C.) |
|---|---|---|---|---|
| After 19 days storage | 105.2 | 97.2 | 104.2 | 96.8 |
| After 40 days storage | 100.3 | — | 95.9 | — |
| After 96 days storage | 108.0 | 102.2 | 107.0 | 102.7 |
| After 150 days storage | 98.7 | 101.5 | 98.5 | 100.4 |
| After 196 days storage | 98.3 | 99.6 | 96.3 | 96.6 |
| After 375 days storage | 99.6 | 93.3 | 101.3 | 95.3 |

TABLE 3

|  | FD(−) (5° C.) | FD(−) (25° C.) | FD(+) (5° C.) | FD(+) (25° C.) |
|---|---|---|---|---|
| After 23 days storage | 103.2 | 95.6 | 96.9 | 88.6 |
| After 43 days storage | 95.2 | 83.7 | 95.4 | 93.0 |
| After 90 days storage | 92.9 | 75.8 | — | — |
| After 183 days storage | 86.9 | 61.5 | 92.7 | 85.3 |
| After 356 days storage | 80.4 | 47.2 | 89.4 | 84.3 |

Example 2

Examination of Addition Amount of Lactose
Preparation of Dry Yeast Cell Powder

To 75 mL of the Ss concentrate liquid (solid content: 5.0%), 25 mL of a lactose solution having a different concentration was added, whereby stock solutions to be dried containing lactose at 0 to 15% were prepared in a volume of 100 mL each. These stock solutions were treated under the conditions that the inlet temperature was 120° C., the outlet temperature was about 80° C., and the amount of treating the stock solution was 4 mL/min using a two-fluid nozzle-type laboratory spray dryer (SD-1000, Tokyo Likakikai Co., Ltd.). The resulting product including the product adhered to the cyclone section was collected and used as the dry product.

Measurement of Titer

The titers of the stock solutions to be dried and the dry products were measured, and the ratio of the titer per solid content in the dry product to the titer per solid content in the stock solution to be dried (residual titer ratio) was calculated. The obtained results are shown in Tables 4 and 5, and FIG. 3.

TABLE 4

|  | SD-5 | SD-6 | SD-7 | SD-8 | SD-9 | SD-10 |
|---|---|---|---|---|---|---|
| Concentration of lactose (%) | 0 | 0.1 | 0.2 | 0.5 | 1 | 2 |
| Residual titer ratio (%) | 34.4 | 42.7 | 49.1 | 72.1 | 77.5 | 83.2 |

TABLE 5

|  | SD-11 | SD-12 | SD-13 | SD-14 |
|---|---|---|---|---|
| Concentration of lactose (%) | 3 | 5 | 10 | 15 |
| Residual titer ratio (%) | 86.8 | 93.4 | 100.7 | 100.2 |

Figure 3:
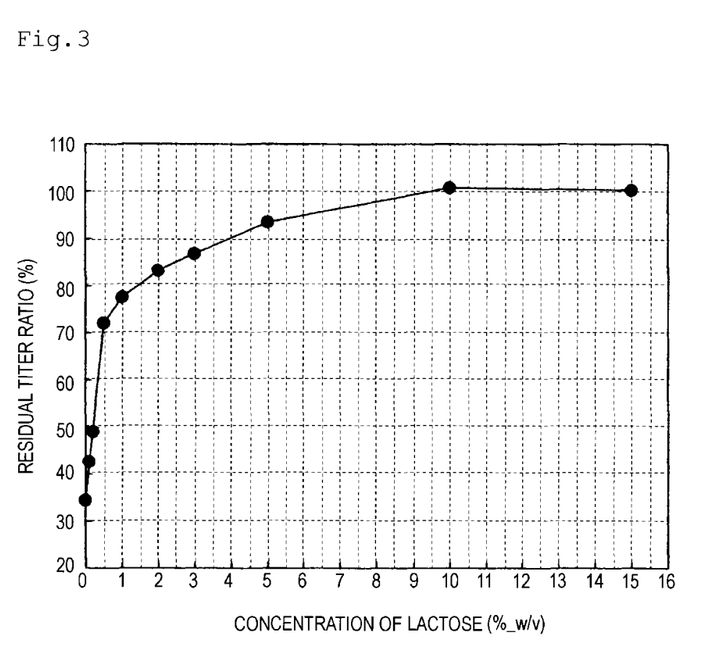
FIG. 3 is a view showing a residual titer ratio after spray drying for spray-dried products.

From the results shown in Tables 4 and 5, and FIG. 3, the residual titer ratio serving as the index of the yield of titer in the whole drying step was increased as the concentration of lactose was increased, and an effect was observed at a concentration of 0.1% or more, and a clear effect was observed at a concentration of 0.5% or more.

Example 3

Examination of Other Stabilizing Agents
(Preparation of Dry Yeast Cell Powder)

An effect of maintaining the enzyme titer when spray drying (stabilizing effect) was compared among dextrins (NSD #300, #500, both from San-ei Sucrochemical Co., Ltd.), maltose, and lactose. To 75 mL of the Ss concentrate liquid (solid content: 5.00), 25 mL of a stabilizing agent solution at 4, 20, or 40% was added, whereby stock solutions to be dried containing the stabilizing agent at 1, 5, or 10% were prepared in a volume of 100 mL each. These stock solutions were treated under the conditions that the inlet temperature was 120° C., the outlet temperature was about 80° C., and the amount of treating the stock solution was 4 mL/min using a two-fluid nozzle-type laboratory spray dryer (SD-1000, Tokyo Likakikai Co., Ltd.). The resulting product including the product adhered to the cyclone section was collected and used as the dry product.
(Measurement of Titer)

The titers of the stock solutions to be dried and the dry products were measured, and the ratio of the titer per solid content in the dry product to the titer per solid content in the stock solution to be dried (residual titer ratio) was calculated. The results are shown in Table 6.

TABLE 6

|  |  | Dextrin NSD #300 | Dextrin NSD #500 | Maltose | Lactose |
|---|---|---|---|---|---|
| Concentration of stabilizing agent | 1% | 50.4 | 44.6 | 61.3 | 77.5 |
|  | 5% | 65.9 | 70.5 | 91.4 | 93.4 |
|  | 10% | 65.4 | 53.4 | 90.5 | 100.7 |

The residual titer ratio was higher in the case where the stabilizing agent coexisted than in the case where the stabilizing agent was not added (34.4%, Table 4). In particular, the residual titer ratio was higher in the case of the disaccharides such as lactose and maltose than in the case of the dextrins, and further, the residual titer ratio was higher in the case of lactose between the disaccharides, and it was found that lactose was superior as the stabilizing agent.

Example 4

Examination of Sugar Composition
(Preparation of Dry Yeast Cell Powder)

Three mixtures were prepared by adding 2.6 L of a 20% lactose solution to 7.8 L of the Ss concentrate liquid (solid content: 5.3%), followed by mixing well. Then, a reaction was allowed to proceed while maintaining the mixtures under the following conditions: 10° C. for 1 hour; 5° C. for 40 hours; and 40° C. for 18 hours, respectively, whereby stock solutions to be dried having a different sugar composition were prepared. These stock solutions were dried under the conditions that the inlet temperature was 120° C., the outlet temperature was about 80° C., the rotation speed of the atomizer was 12500 rpm, and the amount of treating the stock solution was 4 kg/hr using a pilot apparatus (PRODUCTION MINOR, GEA Process Engineering, Inc.).
(Analysis of Sugar Composition)

The sugar composition in the stock solutions to be dried after the reaction was analyzed under the following HPLC conditions. The results are shown in Table 7.
<HPLC Conditions>
Column: Shodex SUGAR KS-802 (Showa Denko K.K.)
Solvent: pure water
Flow rate: 0.5 mL/min
Temperature: 80° C.
Detector: Differential refractometer
(Measurement of Titer)

The titers of the stock solutions to be dried and the dry products were measured, and the ratio of the titer per solid content in the dry product to the titer per solid content in the stock solution to be dried (residual titer ratio) was calculated. The results are shown in Table 7.

TABLE 7

| Reaction conditions | Sugar composition (%) | | | Residual titer ratio (%) |
|---|---|---|---|---|
|  | Tri- or higher oligosaccharide | Disaccharide | Monosaccharide |  |
| 10° C., 1 hour | 7.3 | 84.5 | 8.2 | 96.9 |
| 5° C., 40 hours | 25.0 | 43.8 | 31.2 | 91.3 |
| 40° C., 18 hours | 0.2 | 12.4 | 87.4 | 96.0 |

From the results shown in Table 7, it was found that an effect of stabilizing the titer was exhibited regardless of the degree of the reaction between lactose and β-galactosidase. It was also confirmed that as the stabilizing agent, a monosaccharide (glucose or galactose) or a galactooligosaccharide could be used.

Example 5

Examination of Drying Temperature
(Preparation of Dry Yeast Cell Powder)

To the Ss concentrate liquid (solid content: 5.0%), a 5 N sodium hydroxide solution was added to adjust the pH thereof to 4.5, and by maintaining the liquid at 45° C. for 9 hours, the Ss was killed. To 8 L of this liquid, 2 L of a 25% lactose solution was added and mixed well, whereby a stock solution to be dried was prepared. Then, spray drying was performed for the stock solution by setting the inlet temperature of a drying chamber to 120° C., 150° C., or 180° C. and adjusting the feeding amount of the stock solution so that the outlet temperature of the drying chamber was 80° C.
(Measurement of Titer)

The titers of the stock solution to be dried and the dry products were measured, and the ratio of the titer per solid content in the dry product to the titer per solid content in the stock solution to be dried (residual titer ratio) was calculated. The results are shown in Table 8.

TABLE 8

|  | 120° C. | 150° C. | 180° C. |
|---|---|---|---|
| Residual titer ratio (%) | 103.6 | 96.8 | 90.7 |
| Feeding amount of stock solution (kg/hr) | 3.6 | 10.0 | 12.9 |

From the results shown in Table 8, by increasing the inlet temperature when drying, the feeding amount of the stock solution could be increased, and in the case where the inlet temperature was 180° C., the feeding amount of the stock solution could be increased to about 3.5 times that in the case where the inlet temperature was 120° C. Further, even if the inlet temperature when drying was set to 180° C., 90% or more of the titer of the dry product was maintained, and therefore, it was found that the dry yeast cell powder could be obtained with high economic efficiency at this temperature.

Example 6

Examination of Yeast Other than Ss
(Preparation of Dry Yeast Cell Powder)

Each of *Cryptococcus laurentii* (*C. laurentii* IFO 18803), *Rhodotorula lactosa* (*R. lactosa* JCM 1546), *Sirobasidium magnum* (*S. magnum* JCM 6876), and *Rhodotorula minuta* (*R. minuta* JCM 8101) was separately cultured aerobically at 26° C. in a medium (pH 5) containing lactose (5%), yeast extract (0.3%), monopotassium phosphate (0.1%), and magnesium sulfate (0.05%). This culture solution was centrifuged (10000 G, 30 mins) to obtain wet cells, and sterilized tap water was added thereto and the wet cells were well suspended therein. The resulting suspension was centrifuged under the same conditions, and the obtained wet cells were suspended in a small amount of tap water, and the thus obtained suspension was used as a cell concentrate liquid (solid content: about 4%).

To 75 mL of the cell concentrate liquid, 25 mL of a 20% lactose solution was added, and the resulting mixture was stirred well, whereby a stock solution to be dried was obtained. This procedure was performed at 20° C. or lower. By using this stock solution to be dried, and also a stock solution to be dried prepared by using water in place of the lactose solution, a yeast powder was prepared by a spray drying method. The solid content (calculated value) in the stock solution to be dried was adjusted such that the stock solution contained the microbial cells at about 3% and lactose at about 5%.

The spray drying was performed by using a two-fluid nozzle-type spray dryer (SD-1000) manufactured by Tokyo Likakikai Co., Ltd. under the conditions that the inlet temperature of a drying chamber was 120° C. and the outlet temperature thereof was 70 to 90° C.

(Measurement of Titer)

The titers of the stock solutions to be dried of the respective yeast strains and the dry products were measured, and the ratio of the titer per solid content in the dry product to the titer per solid content in the stock solution to be dried (residual titer ratio) was calculated. Further, the titer of the cell concentrate liquid to which lactose was not added was also measured in the same manner, and the residual titer ratio was calculated. The results are shown in Table 9.

TABLE 9

| Concentration of lactose (w/v %) | C. laurentii (IFO 18803) | R. lactosa (JCM 1546) | S. magnum (JCM 6876) | R. minuta (JCM 8101) |
| --- | --- | --- | --- | --- |
| 0 | 61.5% | NT | 63.9% | 81.3% |
| 5 | 77.1% | 99.8% | 74.0% | 116.1% |

NT: not tested

In the case of the three strains other than *Rhodotorula lactosa* (*R. lactosa*), the residual titer ratio after spray drying was increased by the addition of lactose at 5% as compared with the case where lactose was not added. In the case of *Rhodotorula lactosa*, the residual titer ratio after spray drying when adding lactose at 5% was 99.8%, which was extremely high. From these results, it was shown that an effect of suppressing a decrease in β-gal titer after spray drying exhibited by the addition of lactose was not specific to Ss, but could be widely applied to yeast strains.

Reference Example

Test for Oligosaccharide Production
(Preparation of Suspension of Spray-Dried Product)

The dry product obtained in the above-described Example 5 (inlet temperature: 120° C.) in an amount corresponding to 45 U was weighed, and was added to 10 mL of ion exchanged water to suspend the dry product, whereby a suspension was obtained.
(Production Reaction of Oligosaccharides)

To 800 mL of a 60% lactose solution, the total amount of the suspension of the dry product prepared above was added and mixed, and a reaction was allowed to proceed at 65° C. for 22 hours at pH 6. The results obtained by examining the sugar composition at this time are shown in Table 10.

TABLE 10

| Tetra- or higher oligosaccharide | Trisaccharide | Disaccharide | Glc | Gal |
| --- | --- | --- | --- | --- |
| 1.0 | 30.0 | 58.0 | 10.7 | 0.3 |

As apparent from the results shown in Table 10, it was shown that the dry product of the invention (dry microbial cell powder) could be used in the production reaction of oligosaccharides without any practical problems.

INDUSTRIAL APPLICABILITY

The dry yeast cell powder obtained according to the method of the invention can maintain the enzymatic activity of this yeast stably for a long time in a dry state. That is, it can maintain the enzyme titer when drying without much decreasing the enzyme titer even if it is stored at room temperature.

Therefore, when using the enzymatic activity of the yeast, the handling thereof is easy. Further, since the dry yeast cell powder can be stored, it is not necessary to perform production thereof on demand-led basis. Accordingly, the dry yeast cell powder can be advantageously used in the field using the enzymatic activity.

The invention claimed is:

1. A method for producing a dry microbial cell powder maintaining an enzyme titer, the method comprising:
    adding a carbohydrate to a suspension of microbial cells having an enzymatic activity;
    and then drying the suspension,
    wherein the enzymatic activity is β-galactosidase activity,
    wherein the carbohydrate is at least one selected from the group consisting of lactose and maltose,
    wherein the carbohydrate is added in an amount of from 2 to 15 mass/vol % with respect to the amount of the suspension of the microbial cells,
    wherein the microbial cell is a microorganism from a genus selected from the group consisting of genus *Sporobolomyces*, genus *Rhodotorula*, and genus *Sirobasidium*,
    wherein the drying is spray drying, and
    wherein the enzyme titer after the drying is 70% or higher than the enzyme titer before the drying.

2. The method according to claim 1, wherein the carbohydrate is lactose.

3. A dry microbial cell powder, comprising microbial cells having an enzymatic activity and a carbohydrate,
    wherein the cell powder is obtained by a method comprising:
    adding a carbohydrate to a suspension of microbial cells having an enzymatic activity; wherein the carbohydrate is lactose and an amount of the lactose is at least 5 mass/vol % with respect to the amount of the suspension of the microbial cells, and
    then drying the suspension by spray drying,
    wherein 80% or higher of an enzyme titer immediately after drying is maintained after storage at room temperature for 1 year,
    wherein the enzymatic activity is a β-galactosidase activity, and
    the microbial cells are *Sporobolomyces singularis* cells.

* * * * *